US011364354B2

(12) United States Patent
Reevell (10) Patent No.: US 11,364,354 B2
(45) Date of Patent: Jun. 21, 2022

(54) METHOD FOR PROVIDING AN AEROSOL-GENERATING DEVICE, AEROSOL-GENERATING DEVICE AND FLAT AEROSOL-GENERATING ARTICLE FOR USE IN SUCH A DEVICE

(71) Applicant: PHILIP MORRIS PRODUCTS S.A., Neuchatel (CH)

(72) Inventor: Tony Reevell, London (GB)

(73) Assignee: Philip Morris Products S.A., Neuchatel (CH)

( * ) Notice: Subject to any disclaimer, the term of this patent is extended or adjusted under 35 U.S.C. 154(b) by 609 days.

(21) Appl. No.: 16/302,233

(22) PCT Filed: May 24, 2017

(86) PCT No.: PCT/EP2017/062613
§ 371 (c)(1),
(2) Date: Nov. 16, 2018

(87) PCT Pub. No.: WO2017/202953
PCT Pub. Date: Nov. 30, 2017

(65) Prior Publication Data
US 2020/0046023 A1 Feb. 13, 2020

(30) Foreign Application Priority Data
May 25, 2016 (EP) .................................. 16171372

(51) Int. Cl.
*A61M 15/06* (2006.01)
*A24F 40/40* (2020.01)
(Continued)

(52) U.S. Cl.
CPC ............... *A61M 15/06* (2013.01); *A24B 3/14* (2013.01); *A24B 15/167* (2016.11); *A24D 1/20* (2020.01);
(Continued)

(58) Field of Classification Search
CPC .... A24F 40/20; A24F 1/00; A24F 1/24; A24F 3/00; A24F 40/00; A24F 40/42;
(Continued)

(56) References Cited

U.S. PATENT DOCUMENTS 6,234,455 B1 5/2001 Wittek
2009/0293888 A1 12/2009 Williams
(Continued)

FOREIGN PATENT DOCUMENTS

CN 104135881 11/2014
CN 204930383 1/2016
(Continued)

OTHER PUBLICATIONS

Search Report issued in Russia for Application No. 2018145723 dated Jun. 20, 2020 (4 pages). English translation included.
(Continued)

*Primary Examiner* — Alex B Efta
(74) *Attorney, Agent, or Firm* — Mueting Raasch Group (57) ABSTRACT

The method for providing an aerosol-generating device for use with a shape-transformable aerosol-forming substrate comprises providing an aerosol-generating device comprising a device housing comprising a moulding cavity. The moulding cavity at least partially corresponds to a moulding space between a first mould half and a second mould half of a mould, the first mould half and the second mould half being internal surfaces of the device housing. The method further comprises the step of providing a flat aerosol-forming substrate adapted to change shape when pressed into the moulding cavity and being transformed into a non-flat aerosol-forming substrate. The invention also refers to a flat aerosol-generating article and a kit comprising a flat aerosol-generating article and an aerosol-generating device.

12 Claims, 6 Drawing Sheets

(51) Int. Cl.
  *A24F 40/46* (2020.01)
  *A24F 40/20* (2020.01)
  *A24B 3/14* (2006.01)
  *A24B 15/167* (2020.01)
  *B01J 13/00* (2006.01)
  *A24D 1/20* (2020.01)

(52) U.S. Cl.
  CPC .............. *A24F 40/40* (2020.01); *A24F 40/46* (2020.01); *B01J 13/0095* (2013.01); *A24F 40/20* (2020.01)

(58) Field of Classification Search
  CPC . A24F 40/46; A61M 15/0028; A61M 15/003; A61M 15/0023; A61M 15/06; A24B 15/167
  See application file for complete search history.

(56) References Cited

U.S. PATENT DOCUMENTS

| | | | |
|---|---|---|---|
| 2013/0298905 A1* | 11/2013 | Levin | A24F 40/00 128/202.21 |
| 2014/0060554 A1 | 3/2014 | Collett | |
| 2014/0182608 A1 | 7/2014 | Egoyants | |
| 2015/0163859 A1 | 6/2015 | Schneider | |
| 2016/0295922 A1* | 10/2016 | John | B05D 7/24 |
| 2016/0360785 A1* | 12/2016 | Bless | A24F 40/40 |
| 2018/0310623 A1* | 11/2018 | Batista | A24D 1/20 |

FOREIGN PATENT DOCUMENTS

| | | | |
|---|---|---|---|
| CN | 109152896 | 1/2019 | |
| EP | 0472367 | 3/1996 | |
| EP | 3166427 | 1/2016 | |
| EP | 3166430 | 1/2016 | |
| EP | 3364796 | 4/2017 | |
| EP | 3166425 | 6/2018 | |
| GB | 2529201 | 2/2016 | |
| JP | 2008212205 | 9/2018 | |
| SU | 1836039 | 8/1993 | |
| WO | WO 2015/035510 | 3/2015 | |
| WO | WO 2015/114325 | 8/2015 | |
| WO | WO 2015/114328 | 8/2015 | |
| WO | WO-2015114325 A1 * | 8/2015 | ............ A61M 15/06 |
| WO | WO 2016/050873 | 4/2016 | |

OTHER PUBLICATIONS

PCT International Search Report and Written Opinion for PCT/EP2017/062613 dated Jul. 24, 2017 (11 pages).
Office Action issued in China for Application No. 201780031393.4 dated Aug. 4, 2020 (14 pages). English translation included.

* cited by examiner

METHOD FOR PROVIDING AN AEROSOL-GENERATING DEVICE, AEROSOL-GENERATING DEVICE AND FLAT AEROSOL-GENERATING ARTICLE FOR USE IN SUCH A DEVICE

This application is a U.S. National Stage Application of International Application No. PCT/EP2017/062613 filed May 24, 2017, which was published in English on Nov. 30, 2017, as International Publication No. WO 2017/202953 A1. International Application No. PCT/EP2017/062613 claims priority to European Application No. 16171372.2 filed May 25, 2016.

The invention relates to a method for providing an aerosol-generating device for use with a shape-transformable aerosol-forming substrate and a flat aerosol-generating article for use in such a device. The invention also refers to a kit for an aerosol-generating system comprising an aerosol-generating device and a flat aerosol-generating article.

Various aerosol-generating devices using aerosol-forming substrate, which is heated rather than combusted are known. Aerosol-forming substrate used in such devices typically has a rod-shape imitating the shape of common smoking articles and providing a large vaporization surface. However, these substrates or articles comprising the substrates are not optimized for storing.

Thus, it would be desirable to have an aerosol-generating article, which requires little space for storing and which provides a large surface for aerosol-formation. It would also be desirable to have an aerosol-generating device adapted for use with such an article and a method to provide an aerosol-generating device for use with such an article.

Thus, according to the invention, there is provided a method for providing an aerosol-generating device for use with a shape-transformable aerosol-forming substrate. The method comprises the step providing an aerosol-generating device comprising a device housing comprising a moulding cavity. The moulding cavity at least partially corresponds to a moulding space between a first mould half and a second mould half of a mould, wherein the first mould half and the second mould half are internal surfaces of the device housing. The method further comprises the step of providing a flat aerosol-forming substrate adapted to change shape when pressed into the moulding cavity and being transformed into a non-flat aerosol-forming substrate. The method may comprise the steps of opening the device housing, thereby opening the first and second mould halves and positioning the flat aerosol-forming substrate in between the first and second mould halves. Yet a further step may comprise closing the device housing, thereby closing the first and second mould halves, and thereby transforming the flat aerosol-forming substrate into the non-flat aerosol-forming substrate. The non-flat aerosol-forming substrate preferably has a shape corresponding to the non-flat moulding space in the mould upon closing of the mould.

A flat aerosol-forming substrate is provided, which may be easy and cost efficient to manufacture and to stack and store in a space saving manner. Individual packaging is simplified, which may keep the product longer fresh and may reduce damage during transport. In particular, the aerosol-forming substrate may be a tobacco containing aerosol-forming substrate, preferably a solid tobacco containing aerosol-forming substrate.

The transformability of the shape of the aerosol-forming substrate from a flat shape into a non-flat, for example three-dimensional geometric form, may facilitate the manufacture of small devices, preferably without reducing a total surface of or amount of aerosol-forming substrate. Due to the transformability, the flat substrate may be large and provide a large surface area for substances to be vaporized even in relatively small cavities provided for receiving the aerosol-forming substrate. Preferably, the flat substrate has a dimension larger than a dimension of the device itself, for example larger than a dimension of a moulding cavity for receiving the aerosol-forming substrate or larger than a dimension of a mould. For example, the flat substrate may have a width or length or diameter, which is larger than a diameter or lateral extension of a device housing, larger than a width or length or diameter of a moulding cavity or larger than a diameter or width or length of a mould.

The flat substrate may basically be regarded as substantially two-dimensional, theoretically neglecting a thickness of the substrate. The term 'flat' substrate or 'flat' article is used throughout the specification to refer to a substrate or article that is in the form of a substantially two dimensional topological manifold. Thus, the flat substrate or flat article extends in two dimensions along a surface substantially more than in a third dimension. In particular, the dimensions of the flat substrate or flat article in the two dimensions within the surface is at least 5 times larger than in the third dimension, normal to the surface. An example of a flat substrate or flat article is a structure between two substantially parallel imaginary surfaces, wherein the distance between these two imaginary surfaces is substantially smaller than the extension within the surfaces. Preferably, the flat substrate or the flat article comprising the substrate is planar.

Through the transformation of the substrate upon preparing the device, the flat substrate is moulded in the mould of the device to its final non-flat shape. By the moulding process, the flat substrate is deformed and shaped to extend also into the third dimension. Thus a lateral extension of the flat substrate is reduced in favour of an extension in the third dimension. Upon closing the mould halves, the reduction of the lateral dimension of the flat substrate due to its deformation, allows the use of larger substrates than seem to fit into the mould or into the moulding cavity or even into the device, respectively.

A flat aerosol-forming substrate may have a thickness in a range between 0.2 millimeter and 6 millimeter, preferably, between 0.5 millimeter and 4 millimeter, for example between 0.2 millimeter and 2 millimeter or between 0.4 millimeter and 4 millimeter.

Throughout this application, whenever a value is mentioned, this is to be understood such that the value is explicitly disclosed. However, a value is also to be understood as not having to be exactly the particular value due to technical considerations.

The aerosol-forming substrate or aerosol-generating article comprises a flexibility such as to be transformable in a non-flat shape. Preferably, substrate and article comprise a flexibility such as to not break or be ruptured upon transformation. Preferably, transformation excludes a folding of the substrate or article onto itself. Preferably, the substrate is not bent by more than 135 degrees upon moulding, more preferably by not more than 90 degree upon being moulded in the mould.

The flat substrate may be provided in the form of a single sheet of aerosol-forming substrate or may be provided in a folded form such as to still form a flat substrate. In the mould of the device, a single sheet may be transformed into a three-dimensional geometrical form, for example, into a cone-like shape, a rippled sheet, an undulating corrugated sheet or a hollow or full rod or rods. In the mould of the device, a folded flat substrate is unfolded to form a non-flat substrate, for example, is unfolded into a tubular-shape or a cone-like shape.

The moulding of the aerosol-forming substrate upon preparing a device for use, also guarantees a very efficient heating since the aerosol-forming substrate is pressed against a heating element preferably arranged in the mould.

The method according to the invention may comprise the steps of providing a device housing comprising a mouthpiece and a body portion. The body portion comprises a first internal surface having a shape comprising a frustum. The mouthpiece comprises a second internal surface having a shape corresponding to the shape of the first internal surface of the body portion, for example, comprising a corresponding frustum. The first and second internal surface form the first and second mould halves with the moulding space in the form comprising a hollow frustum. Yet further method steps comprise providing a mechanism for accessing and securing the mould such that upon accessing, the mould is opened and the flat aerosol-forming substrate may be placed in the mould, and such that upon securing the mould is closed and the flat aerosol-forming substrate is transformed into a non-flat aerosol-forming substrate having a shape comprising a hollow frustum. Accessing the mould is provided by an at least partial disassembly of mouthpiece and body portion. Securing the mould may be provided by an assembly or reassembly of mouthpiece and body portion, accordingly. In a partial disassembly, mouthpiece and body portion are not completely separated. A partial disassembly may, for example, comprise a hinged connection between mouthpiece and body portion. Preferably, mouthpiece and body portion are completely disassembled for accessing the mould.

The method transforming flat substrates into shapes comprising a frustum facilitates the use of rather large flat aerosol-forming substrates, having a diameter of a mould, typically even larger than an outer diameter of the device. The transformed substrates may have a shape comprising a frustum, for example may have a cone shape, which shape has proven to be efficient in aerosol formation and convenient in use and handling in aerosol-generating devices. Such substrate forms may be heated in a very efficient manner, for example along an entire frustum side wall. Such substrate forms may also be removed from a device in a simple manner, for example not requiring contact with the used substrate.

In addition, the method allows the manufacture of devices with an as such known set-up comprising mouthpiece and body portion, wherein the substrate or an article comprising the substrate is placed between the two device parts.

As used herein, the term 'aerosol-generating device' is used to describe a device that is configured for interaction with an aerosol-forming substrate to generate an aerosol. The aerosol-generating device may be a hand-held device. Preferably, the aerosol-generating device is a puffing device for generating an aerosol that is directly inhalable by a user thorough the user's mouth. Most preferably, the aerosol-generating device is configured for use with an aerosol-generating article comprising an aerosol-forming substrate, in particular for use with an aerosol-generating article according to the invention and as described herein.

A heating in the device may be provided in the body portion or in the mouthpiece. The heating may, for example, be resistive or inductive. The heating may be provided for heating the first or the second mould half. The heating may, for example, be incorporated into any of the mould halves. One or several heating elements may be provided for heating the aerosol-forming substrate. Several heating elements may be provided for a selective, for example, a sequential heating of substrate sections.

According to the invention, there is also provided an aerosol-generating device comprising a device housing comprising a moulding cavity for receiving an aerosol-forming substrate. The moulding cavity at least partially corresponds to a moulding space between a first and a second mould half of a mould. The first mould half and the second mould half are internal surfaces of the device housing. In an open state of the mould, which open state corresponds to an open device housing, the aerosol-generating device is adapted to receive a flat aerosol-forming substrate in between the first and second mould halves. In a closed state of the mould, which closed state corresponds to a closed device housing, the moulding space in between the first and second mould halves has a non-flat shape.

The first mould half and the second mould half may have corresponding shapes, for example the internal surfaces of the device housing may be formed such that a first mould half may be a cavity and a second mould half may be a correspondingly formed protrusion or vice versa. First and second mould halves may also have the same shape. For example the first mould half may be a cavity and the second mould half may be a cavity as well.

The first and second mould halves are adapted to transform a flat aerosol-forming substrate supplied between the first and second mould halves into a non-flat aerosol-forming substrate having a shape corresponding to the non-flat moulding space in the mould upon closing of the mould, which is preferably directly correlated with a closing of the device housing.

One of the first or second mould halves may comprise a heating element for heating the transformed non-flat aerosol-forming substrate.

The device housing may comprise a mouthpiece and a body portion. The body portion may comprise a heating element arranged on a first internal surface having a shape comprising a frustum. The mouthpiece may comprise a second internal surface having a shape corresponding to the first internal surface of the body portion. The first and second internal surface form the first and second mould halves, wherein in an assembled state of mouthpiece and body portion the mould is in a closed position forming the moulding space in between the mould halves in the form comprising a hollow frustum. The mould halves are adapted to transform a flat aerosol-forming substrate supplied between the mould halves into a non-flat aerosol-forming substrate having a shape comprising a hollow frustum.

The first internal surface and the second internal surface may be formed such that the flat aerosol-forming substrate is transformed into a hollow frustum-shaped or into a hollow cone-shape substrate upon assembly of the body portion and the mouthpiece.

The first internal surface of the body portion may be formed as a cavity comprising the shape of an inverse frustum. Then, the second internal surface of the mouthpiece is formed as a protrusion comprising the shape of frustum or vice versa. Thus, the first internal surface may correspond to a male mould half comprising a frustum protruding from the device body along a longitudinal axis of the device body, and the second internal surface of the mouthpiece may correspond to a female mould half comprising an inverse frustum, or vice versa.

A frustum of an internal surface may, for example, be circularly conical-shaped, pyramid shaped or may be of star-shape. Preferably, the inverse frustum of the corresponding other internal surface may be inverse circularly conical-shaped, inverse pyramid shaped or may be of inverse star-shape.

The aerosol-generating device may comprise alignment elements for aligning an aerosol-forming substrate between the mouthpiece and the body portion, or for aligning the mouthpiece and the body portion upon assembly of the device housing, or for aligning both the aerosol-forming substrate between the mouthpiece and the body portion and for aligning the mouthpiece and the body portion upon assembly of the device housing.

Any one or all of the aerosol-forming substrate, the body portion or the mouthpiece may comprise alignment elements.

Preferably, alignment elements are symmetrically arranged in the device housing or the substrate, for example on body portion and the mouthpiece. Alignment elements may be central alignment elements arranged in a center of the device, for example on a central longitudinal axis of the device. Alignment elements may be circumferential elements arranged along a circumference of the mouthpiece and of the body portion.

The device may be provided with connection elements, allowing a detachable assembly of the mouthpiece and the body portion. Connection elements may, for example, be embodied as form fit, as clamps, as magnetic fasteners or as snap fit.

Alignment elements may be embodied as connection elements or connection element may be embodied as alignment elements.

An airflow channel may be provided through the moulding cavity, preferably, along a longitudinal direction of the device housing, in particular along a longitudinal extension of the moulding cavity. The airflow channel may be provided to pass through the mould, for example between the first and second mould half. The airflow channel may be provided to pass through the mould only.

A plurality of airflow channels may be provided through the moulding cavity, in particular through the mould. Individual airflow channels may, for example be provided to let air or aerosol pass through a portion only of the aerosol-forming substrate.

In the aerosol-generating device an internal surface forming a mould half may be provided with a plurality of openings. The plurality of openings enables aerosol to leave the mould through the internal surface of the mould half provided with the plurality of openings. The plurality of openings may be provided in the form of, for example, micro-perforations or a porous material. The plurality of openings in an internal surface forming a mould half may substantially be the only path for an aerosol formed by heating the substrate in the mould to leave the mould and an airflow to pass through the mould. However, additional air-flow channels may be arranged in the mould or in a moulding cavity comprising the mould to let air into the mould or moulding cavity and let aerosol and air leave the mould.

One or several airflow channels or open mould surfaces may be provided to let an airflow pass through the mould or moulding cavity. However, one or several airflow channels or open mould surfaces may also be provided to enhance an airflow over an aerosol-forming substrate to enlarge a space or enable a sufficient amount of aerosol to be released into an airflow path for being transported downstream in the device.

As used herein, the term 'aerosol-forming substrate' refers to a substrate that is capable of releasing volatile substances to form an inhalable aerosol therefrom. The aerosol-forming substrate may comprise a tobacco-containing material containing volatile tobacco flavour compounds, which are released from the substrate upon heating. In particular, the aerosol-forming substrate may be a tobacco containing aerosol-forming substrate, preferably a solid tobacco containing aerosol-forming substrate. Alternatively, the aerosol-forming substrate may comprise a non-tobacco material. The aerosol-forming substrate may further comprise an aerosol former. Examples of suitable aerosol formers are glycerine and propylene glycol.

The aerosol-forming substrate may comprise, for example, one or more of: powder, granules, pellets, shreds, spaghetti strands, strips or sheets containing one or more of: herb leaf, tobacco leaf, fragments of tobacco ribs, reconstituted tobacco, homogenised tobacco, extruded tobacco and expanded tobacco.

Optionally, the aerosol-forming substrate may contain additional tobacco or non-tobacco volatile flavour compounds, to be released upon heating of the aerosol-forming substrate. The aerosol-forming substrate may also contain micro-capsules that, for example, include the additional tobacco or non-tobacco volatile flavour compounds and such micro-capsules may melt during heating of the solid aerosol-forming substrate.

The aerosol-forming substrate may comprise a sheet of homogenised tobacco material that has been formed or cut into a desired shape of flat piece of aerosol-forming substrate.

The aerosol-forming substrate may be substantially disc shaped. The aerosol-forming substrate may be substantially rectangular.

Tobacco containing slurry and a tobacco sheet forming the aerosol-forming substrate made from the tobacco containing slurry comprises tobacco particles, fiber particles, aerosol former, binder and for example also flavours.

Preferably, the aerosol-forming tobacco substrate is a tobacco sheet comprising tobacco material, fibers, binder and aerosol former. Preferably, the tobacco sheet is a cast leaf. Cast leaf is a form of reconstituted tobacco that is formed from a slurry including tobacco particles, fiber particles, aerosol former, binder and for example also flavours.

Tobacco particles may be of the form of a tobacco dust having particles in the order of 30 micrometers to 250 micrometers, preferably in the order of 30 micrometers to 80 micrometers or 100 micrometers to 250 micrometers, depending on a desired sheet thickness and casting gap, where the casting gap typically defines the thickness of the sheet, preferably corresponding to the thickness of the aerosol-generating article or half of the thickness of the aerosol-generating article in case of a folded article.

Fiber particles may include tobacco stem materials, stalks or other tobacco plant material, and other cellulose-based fibers such as wood fibers having a low lignin content.

Fiber particles may be selected based on the desire to produce a sufficient tensile strength for the sheet versus a low inclusion rate, for example, an inclusion rate between approximately 2 percent to 15 percent. Alternatively, fibers, such as vegetable fibers, may be used either with the above fiber particles or in the alternative, including hemp and bamboo.

Aerosol formers included in the slurry for forming the cast leaf may be chosen based on one or more characteristics. Functionally, the aerosol former provides a mechanism that allows it to be volatilized and convey nicotine or flavouring or both in an aerosol when heated above the specific volatilization temperature of the aerosol former. Different aerosol formers typically vaporize at different temperatures. An aerosol former may be chosen based on its ability, for example, to remain stable at or around room temperature but able to volatize at a higher temperature, for example, between 40 degree Celsius and 450 degree Celsius. The aerosol former may also have humectant type properties that help maintain a desirable level of moisture in an aerosol-forming substrate when the substrate is composed of a tobacco-based product including tobacco particles. In particular, some aerosol formers are hygroscopic material that function as a humectant, that is, a material that helps keep a substrate containing the humectant moist.

One or more aerosol former may be combined to take advantage of one or more properties of the combined aerosol formers. For example, triacetin may be combined with glycerol and water to take advantage of the triacetin's ability to convey active components and the humectant properties of the glycerol.

Aerosol formers may be selected from the polyols, glycol ethers, polyol ester, esters, and fatty acids and may comprise one or more of the following compounds: glycerol, erythritol, 1,3-butylene glycol, tetraethylene glycol, triethylene glycol, triethyl citrate, propylene carbonate, ethyl laurate, triacetin, meso-Erythritol, a diacetin mixture, a diethyl suberate, triethyl citrate, benzyl benzoate, benzyl phenyl acetate, ethyl vanillate, tributyrin, lauryl acetate, lauric acid, myristic acid, and propylene glycol.

The aerosol-forming substrate or the aerosol-forming slurry forming the substrate may contain waxes or fats, which waxes or fats are added for a low temperature release of aerosol-forming substances from the solid aerosol-forming substrate. Some waxes and fats are known for their ability to lower the temperature where an aerosol former is released from a solid substrate containing said waxes or fats.

Preferably, tobacco containing slurry comprises homogenized tobacco material and comprises glycerol or propylene glycol as aerosol former. Preferably, the aerosol-forming substrate is made of a tobacco containing slurry as described above.

According to the invention, there is further provided a flat aerosol-generating article for use in an aerosol-generating device, in particular for use with an aerosol-generating device according to the invention and as described herein. The flat aerosol-generating article comprises an aerosol-forming substrate and has an at least partially convex circumference. The flat aerosol-generating article is transformable into a conical shape.

The aerosol-generating article may consist of the flat aerosol-forming substrate. The aerosol-generating article may comprise the flat aerosol-forming substrate provided with at least a protective layer. A protective layer may be pervious to substances evaporated from the substrate and is typically not removed before use of the article.

In particular, the aerosol-forming substrate may be a tobacco containing aerosol-forming substrate, preferably a solid tobacco containing aerosol-forming substrate.

The flat article facilitates stacking of the article and simplifies storing and transport of the article.

The flat aerosol-generating article or a stack of aerosol-generating articles may be enveloped with a packaging, which is removed before use of the article(s).

The flat article may comprise at least an alignment opening for aligning the article in a device. The at least one alignment opening may, for example, be any one or a combination of a centrally arranged opening, radially inwardly extending slits or circumferentially arranged slits.

In preferred embodiments, the flat article is disc-shaped. The article may be a disc bound by a circle. The article may be a disc bound by a polygon.

Preferably, the article is rotationally symmetric.

The article may be a disc, possibly comprising one or several alignment openings.

The article may be disc-shaped comprising radially extending fins, for example three to five fins. Upon transforming the flat article into a conical shape, the fins may be aligned next to each other without overlapping or folding of the fins.

The flat article may be a flat folded article, for example a folded right circular cone or a folded frustum, preferably a right frustum, for example in the shape of a circular frustum or a pyramidal frustum. Upon mounting the folded article is unfolded and in the mould brought to its final shape.

A diameter of a disc shaped flat article may, for example, be between 10 millimeter and 40 millimeter, preferably between 20 millimeter and 30 millimeter.

A folded flat article may, for example, be between 10 millimeter and 40 millimeter, preferably between 10 millimeter and 20 millimeter.

A rectangular flat article may, for example, have a length in a range between 30 millimeter and 100 millimeter, preferably between 40 millimeter and 80 millimeter and have a width in a range between 5 millimeter and 40 millimeter, preferably between 10 millimeter and 20 millimeter.

The flat article may comprise a layered structure. The layered structure comprises at least one layer comprising the aerosol-forming substrate and an open layer adapted for aerosol to flow within the layer. An open layer may be a porous layer. Preferably, the open layer comprises a predefined general flow direction for the aerosol and an airflow to flow in the layer. Preferably aerosol is made to flow along a longitudinal, a radial or in a central direction of the article. Preferably, aerosol evaporated from the aerosol-forming substrate layer flows in the open layer and follows the contour of the substrate layer. A predefined general flow direction of the open layer may lead gaseous fluid, typically aerosol, air, evaporated substances or aerosol-containing air into the direction of an outlet of an aerosol-generating device, for example into the direction of a mouthpiece or an outlet opening of the device. An open layer may, for example, be made of a foam or cellulose type material comprising an open cell structure.

The open layer allows aerosol to pass through the article also after transformation into a non-flat shape.

A further layer of the layered structure may be a protective layer covering the at least one layer comprising the aerosol-forming substrate. A protective layer may be pervious to substances evaporated from the substrate and is typically not removed before use of the article. Protective layers may, for example, be paper layers such as cigarette paper, in the form of a top and a bottom layer of the flat aerosol-generating article.

The layered structure may comprise an additional aerosol-forming substrate layer.

An aerosol-generating system may comprise an aerosol-generating device comprising a device housing according to the invention and as described herein. The system further comprises a shape-transformable aerosol-generating article. In a preparation state of the system the transformable aerosol-generating article comprises a flat aerosol-forming substrate. In a ready to be used state of the system the system comprises a non-flat aerosol-generating article comprising a non-flat aerosol-forming substrate transformed through deformation of the flat aerosol-generating article between device housing parts forming first and second mould halves. Preferably, by assembling the device housing parts the first and second mould halves are closed and the substrate is moulded. Preferably, the shape-transformable aerosol-generating article is a flat aerosol-generating article according to the invention and as described herein.

According to the invention, there is yet further provided a kit for an aerosol-generating system. The kit comprises an aerosol-generating device comprising a device housing comprising a moulding cavity. The moulding cavity at least partially corresponds to a moulding space between a first and a second mould half of a mould. The first mould half and the second mould half are internal surfaces of the device housing. The mould has a longitudinal mould extension and a lateral mould extension. The kit further comprises a flat aerosol-generating article comprising a flat aerosol-forming substrate having a longitudinal substrate extension and a lateral substrate extension. The flat aerosol-generating article is configured to be mounted in the moulding cavity in between the first and second mould half of the device housing, and is further configured to be transformed into a non-flat aerosol-forming substrate. Therein the lateral substrate extension is larger than the lateral mould extension or the longitudinal substrate extension is larger than the longitudinal mould extension. The non-flat aerosol-forming substrate preferably has a shape corresponding to the non-flat moulding space in the mould upon closing of the mould.

A longitudinal mould extension is seen in longitudinal direction of the device and the lateral mould extension is seen in lateral direction of the device.

An aerosol-forming substrate may, for example, have a substantially rectangular form and be adapted to be inserted into a moulding cavity of the device housing. Through the moulding process between the moulds, a length or a width or a length and a width of the substrate is thereby reduced such that the original length or width or length and width of the substrate may be larger than a length or width of the mould. Preferably, in these embodiments, the substrate is not larger than a moulding cavity for constructional reasons of a device.

An aerosol-forming substrate may, for example, have a substantially disc-shape form. Through the specific moulding process of a disc-shaped article, the lateral extension of the substrate may be larger than the lateral extension of the mould, may possibly be larger than the lateral extension of the moulding cavity or may even be larger than a diameter of the device housing.

The aerosol-forming substrate may have a lateral substrate extension larger than a lateral extension of the device housing. The lateral extension of the aerosol-forming substrate may, for example, be a diameter of the aerosol-forming substrate, wherein the lateral extension of the mould extends in radial direction of the device housing and may be a diameter of a mould, for example a diameter of a base of a cone.

In embodiments, where disc-shaped articles to be transformed into articles having a shape comprising a frustum such as cones or frusta, or folded cones or folded frusta are used, a lateral extension of the articles or diameters of the articles are preferably larger than a moulding cavity for receiving an aerosol-generating article of the device housing, more preferable larger than the diameter of the device housing.

The aerosol-generating device of the kit may be an aerosol-generating device according to the invention and as described herein.

The aerosol-generating article of the kit may be an aerosol-generating article according to the invention and as described herein.

In particular, the aerosol-forming substrate may be a tobacco containing aerosol-forming substrate, preferably a solid tobacco containing aerosol-forming substrate.

The invention is further described with regard to embodiments, which are illustrated by means of the following drawings, wherein.

Figure 1:
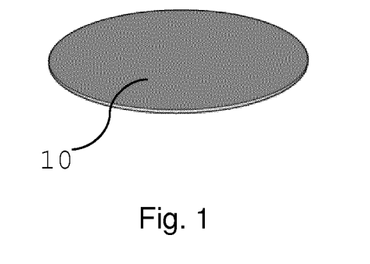
FIG. 1 shows a disc-shaped aerosol-forming substrate.
Figure 2:
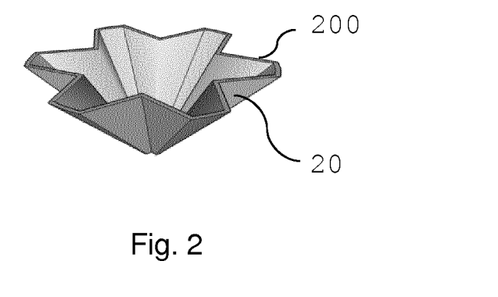
FIG. 2 shows the shape-transformed substrate of FIG. 1.

The flat aerosol-generating article shown in FIG. 1 is a disc 10 of an aerosol-forming substrate, preferably a disc cut from a tobacco containing cast leaf. In the mould of a corresponding aerosol-generating device, the flat disc 1 is transformed into a pyramid 20 having a star-shaped base 200 as illustrated in FIG. 2. The star-shaped form of the mould allows to transform the disc without creating wrinkles and folds in the substrate.

Figure 3:
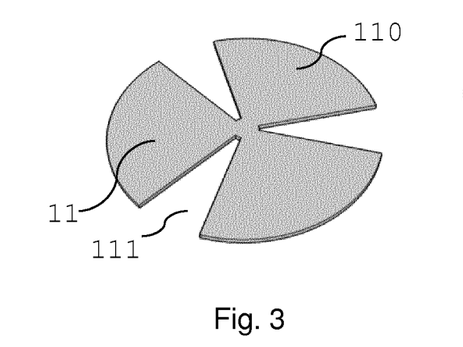
FIG. 3 shows a three-leafed aerosol-forming substrate.
Figure 4:
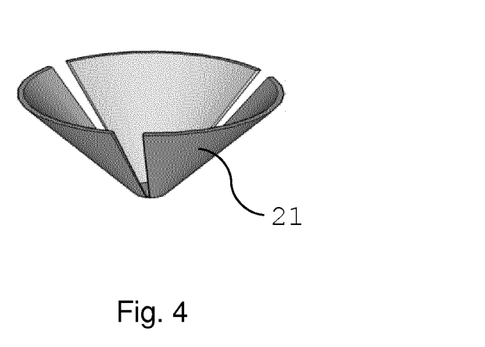
FIG. 4 shows the shape-transformed substrate of FIG. 3.

The flat article shown in FIG. 3 is a three-bladed disc 11 comprising three blades 110 separated by triangularly shaped cut-outs 111 and connected in the center of the disc 11. By a corresponding mould shape the three-bladed disc 11 is formed into a cone comprising a slit side wall 21. In FIG. 4 the side of the cone is not closed. However, depending on the original size of the cut-outs 111 and the form of the mould the article 21 is formed in, two neighbouring blades 110 may become arranged flush after moulding forming a circular right cone. If several heating elements are used to heat the substrate, preferably one blade 110 of the disc 11 is heated by one heating element. Preferably, the article is positioned in a mould such that the slits between the blades 110 are arranged between heating elements.

The cut-outs 111 of the disc 11 may also serve as positioning and alignment means of the article in a device as will be illustrated below.

Figure 5:
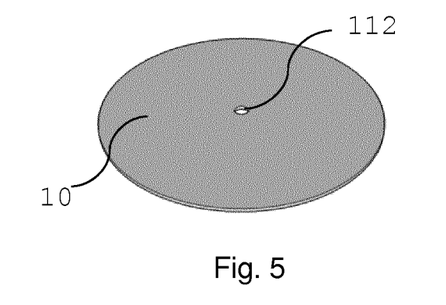
FIGS. 5,6 show other disc-shaped aerosol-forming substrates.
Figure 6:
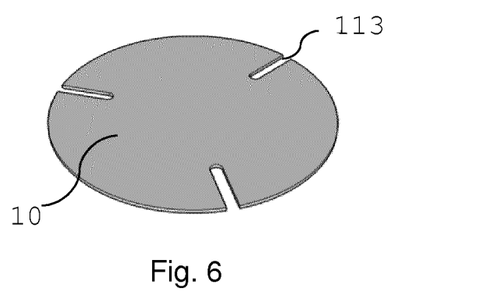

FIG. 5 and FIG. 6 show the disc 10 of FIG. 1, however with positioning and alignment means. In FIG. 5 a centrally arranged opening is provided to interact with a corresponding centrally arranged pin in a cavity for receiving the disc 10. In FIG. 6 three radially inwardly extending slots 113 are arranged equidistantly along the circumference of the disc 10. The slots 113 may interact, for example, with three pins arranged on a circumference of a mould half.

Figure 7:
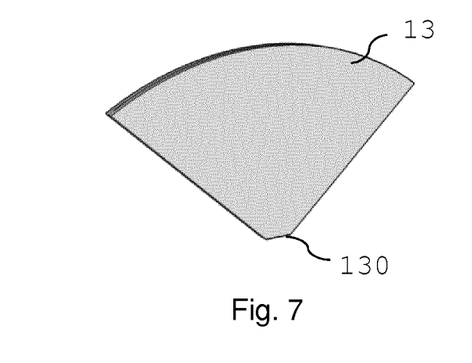
FIGS. 7,8 show a folded and unfolded cone-shaped aerosol-forming substrate.
Figure 8:
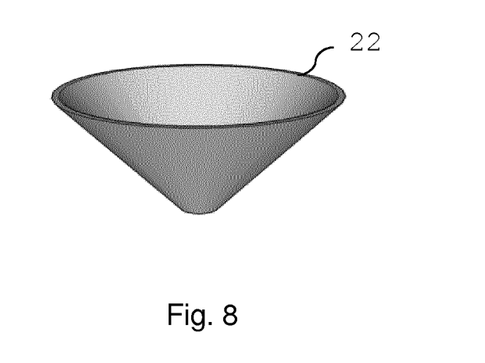

FIG. 7 and FIG. 8 show an example of a folded and unfolded flat aerosol-generating article in the form of a folded frustum 13. The article is basically cone-shaped having a flat top 130. The top 130 may be closed or may be open, for example serving to align the article in a moulding cavity.

Figure 9:
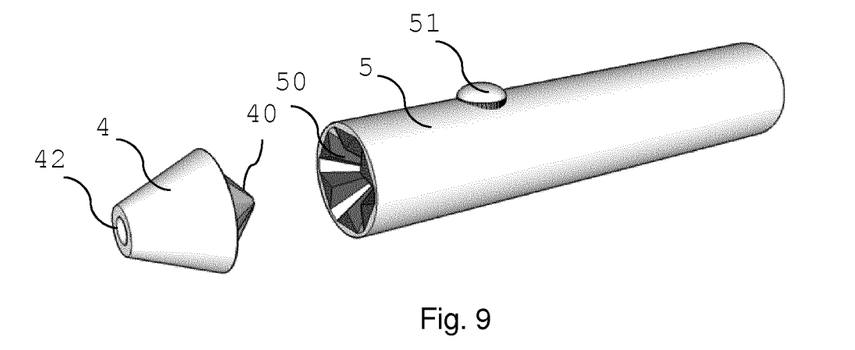
FIG. 9 illustrates an aerosol-generating device.

FIG. 9 shows an aerosol-generating device. The device comprises a body portion 5 and a mouthpiece portion 4 comprising an outlet opening 42. The device is substantially rod-shaped having a substantially circular cross section. The body portion 5 of the device may, for example, comprise a power source such as a battery and electronics for controlling a heating of the device. The body portion 5 is provided with an activation knob 51 for activating the device, for example starting a heating.

In FIG. 9 the body portion 5 comprises a first mould half 50 formed by an internal surface of the body portion 5. The first mould half 50 forms part of a moulding cavity for receiving an aerosol-generating article. The mouthpiece portion 4 comprises a second mould half 40 formed by an internal surface of the mouthpiece portion 4. First and second mould haves correspond to each other and are formed as pyramids having a star-shaped base. The first mould half 50 has the form of a star-shaped inverse pyramid and the second mould half 40 has the form of a corresponding star-shaped pyramid.

Figure 10:
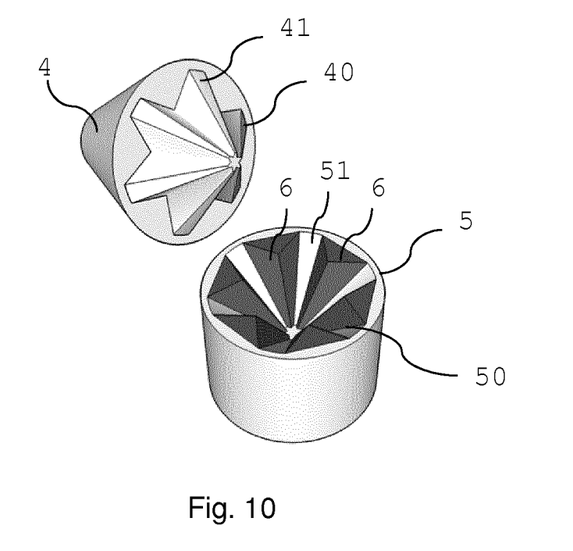
FIG. 10 is an enlarged view of the moulding cavity of the device of FIG. 9.

In FIG. 10 the mould halves are shown in more detail. Several separate heating elements 6 are provided in the first mould half 50 to heat portions of an aerosol-generating article. The heating elements 6 are separated by intermediate sections 51 corresponding to the inverse of the spines 41 of the star-shaped pyramid forming the second mould half 40.

Figure 11:
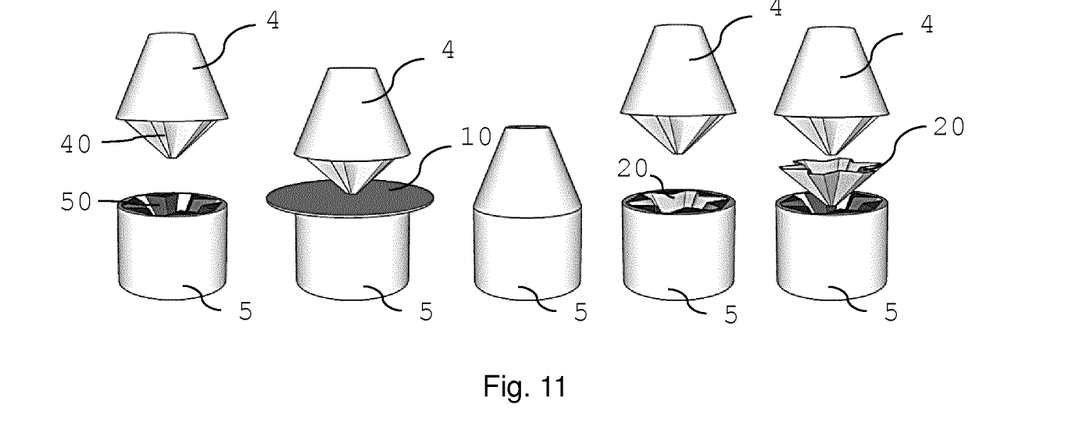
FIG. 11 illustrates a moulding process of a disc-shaped substrate.

In FIG. 11, the moulding process in the device of FIG. 10 and the transformation process of the flat aerosol-forming substrate into a non-flat aerosol-forming substrate is shown with the example of a disc 10 that is transformed into a star-shaped pyramid 20. The flat disc 10 is arranged between mouthpiece portion 4 and body portion 5. Upon closure of the mould, corresponding to an assembly of the device, the disc is formed according to the moulding space between the first and second mould halves 40,50.

After use, the device may be disassembled, the mould is opened and the used substrate 20 may be removed from the mould and the device, accordingly. As is best illustrated in FIG. 11, the disc 10 has a diameter, which is larger than the diameter of the body portion 5 of the device and of the mouthpiece portion 4. The diameter of the disc 10 is about 1.5 times the diameter of the body portion 5.

Figure 12:
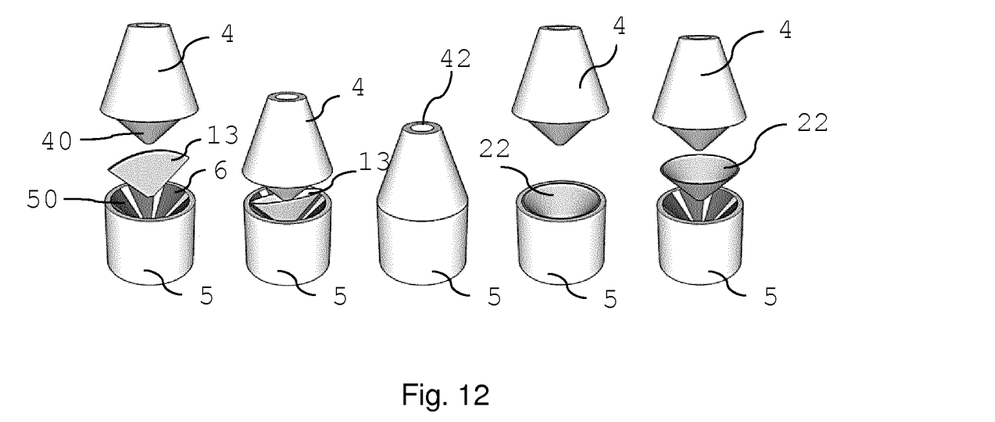
FIG. 12 illustrates a moulding process of a folded substrate.

In FIG. 12 the transformation of a folded aerosol-generating article is illustrated. The article is transformed from a folded 13 into an unfolded 22 circular cone. Upon assembly of mouthpiece 4 and body portion 5, the tip of a cone-shaped first mould half 40 opens the cone by being inserted onto the folded base of the cone 13. The first mould half 50 of the body portion has an inverse circular cone-shape for receiving the article 22. First and second mould halves 40,50, when closed, comprise a cone-shaped moulding space. The article in the folded state has a lateral extension corresponding to the folded width of the base of the cone 13, which lateral extension is larger than the diameter of the mould. According to the geometry of circles, the lateral dimension of the folded cone 13 is about 1.5 times larger than the diameter of the base of the mould.

Heating elements 6 are arranged along the wall of the inverse cone of the second mould half 50 and are indicated by dark triangles interrupted by light triangles.

Figure 13:
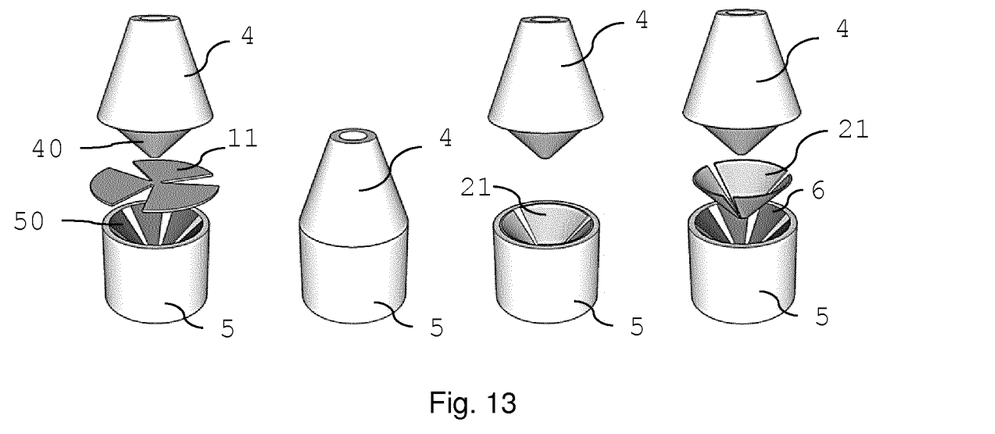
FIG. 13 illustrates a moulding process of a three-bladed substrate.

FIG. 13 illustrates the moulding process of the three-bladed disc 11 of FIGS. 3 and 4 in the same device as shown in FIG. 12.

Figure 14:
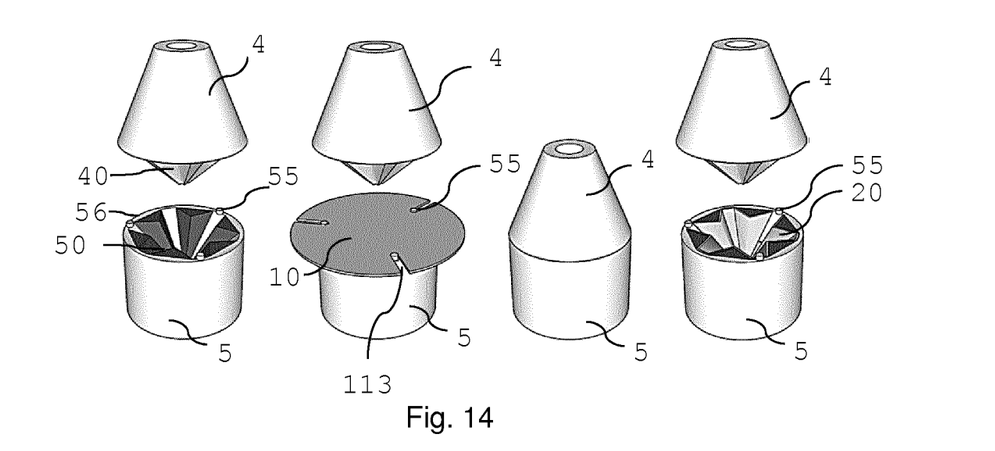
FIG. 14 illustrates a moulding process of a disc-shaped substrate including alignment and connection elements.

In FIG. 14 the alignment and transformation of a disc 10 comprising alignment slots 113 as shown in FIG. 6 is illustrated. Three pegs 55 are regularly arranged on the rim 56 along the circumference of the proximal end of the body portion 5. The disc 10 is laid flat over the first mould half 50 onto the body portion 5 such that the pegs 55 extend into the slots 113. Preferably, a length of the slots 113 is chosen such as to be arranged along a (imaginary) circle corresponding to a same (imaginary) circle the pegs 55 are arranged on. However, for an aligning the slots 113 may also extend further into the direction of the center of the disc 10.

Upon transformation, that is, upon pushing the substrate into the second mould half 50, the disc 20 is guided with the slots 113 along the pegs 55, preventing a rotational displacement of the disc 10 in the mould upon moulding.

Figure 15:
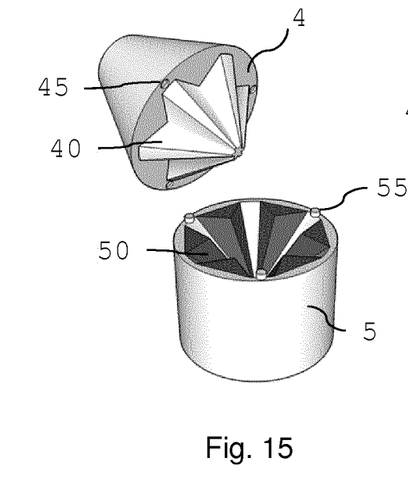
FIG. 15 is an enlarged view of the moulding cavity of FIG. 14.

The device of FIG. 14 basically corresponds to the device of FIG. 11, however provided with alignment pegs 55. The pegs 55 not only serve for aligning the disc 10 in the device but also for aligning mouthpiece portion 4 and body portion 5 upon assembly thereof. As may be seen in FIG. 15 the distal end of the mouthpiece portion 4 comprises three bore holes 45 corresponding to the pegs 55 of the body portion 5. When assembled the combined pegs 55 and holes 45 prevent a relative rotation of mouthpiece and body portion. Pegs 55 and holes 45 may also serve as connection elements. They may be designed as form fit providing a certain force that has to be overcome to disassemble the mouthpiece 4 and body portion 5.

Figure 16:
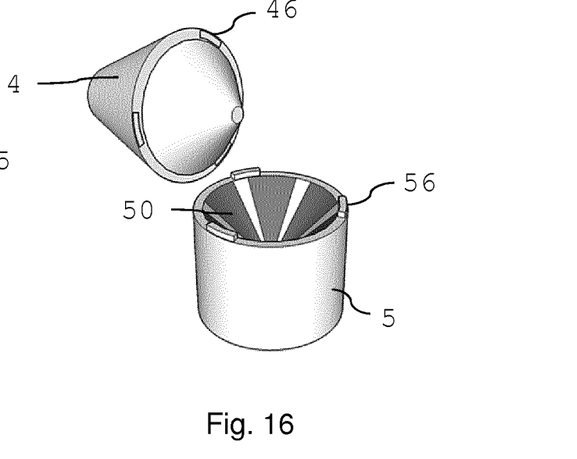
FIG. 16 is an enlarged view of a moulding cavity of a mouthpiece and body portion comprising other alignment and connection elements.
Figure 17:
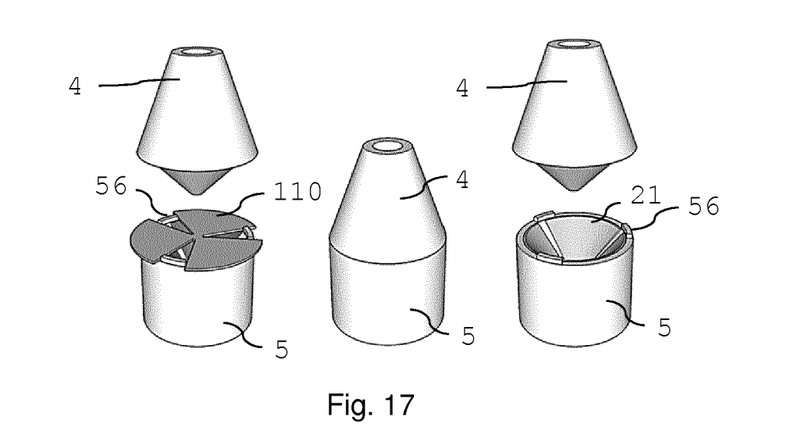
FIG. 17 illustrates a moulding process of a three-bladed substrate in the moulding cavity of FIG. 16.

FIG. 16 and FIG. 17 show another example of alignment elements in the form of longitudinal rim segments 56 protruding in longitudinal direction of the body portion 5. The mouthpiece 4 is provided with corresponding elongate recesses 46.

Such alignment elements are in particular suited for supporting an alignment of a three-bladed disc 11 (e.g. as shown in FIG. 3) over and in a mould. Such alignment elements may support the alignment of blades 110 of the disc 11 on individual heating elements and spaces 111 between blades 110 in between heating elements. Thus, a heating of the aerosol-forming substrate in a mould may be optimized.

According to an amount of blades 110 a bladed disc 10 is provided, the amount and sizes of rim segments 56 may be adapted.

The rim segments 56 and corresponding recesses 46 serve as connection elements for the device.

Figures 18, 19:
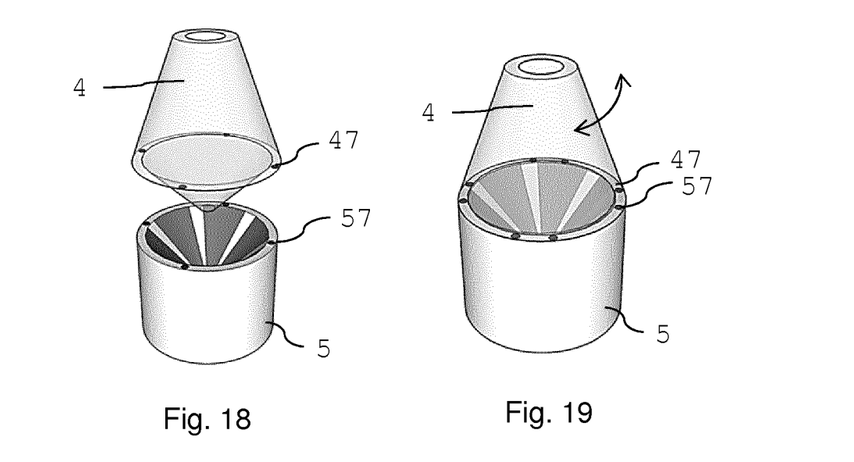
FIGS. 18,19 show mouthpiece and body portion comprising magnetic alignment and connection elements.

FIG. 18 and FIG. 19 show alignment and connection elements in the form of magnetic means. Mouthpiece and body portion 4,5, are provided with magnetic point connections 47,57.

The mouthpiece 4 is drawn in a semi-transparent manner to allow view onto the point connections 47,57.

As mouthpiece 4 and body portion 5 are brought together, the magnetic attraction serves to orient the two parts relative to each other such that they are aligned and connected. Depending on the magnetic force between the point connection 47,57 a pulling force to separate the two parts may be adjusted. For orientation or disconnection of mouthpiece and body portion 4,5 the two parts may be rotated to disconnect the magnetic connections 47,57 (indicated by an arrow).

Figure 20:
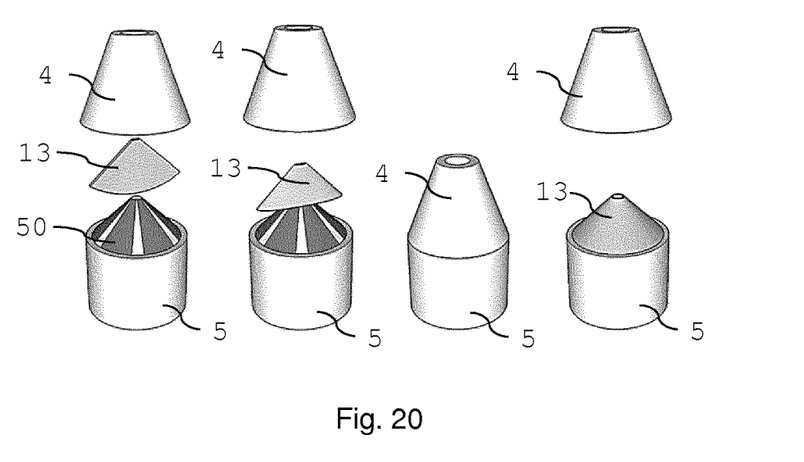
FIG. 20 illustrates a moulding process of a folded article with a protruding cone as mould half of a body portion of a device.
Figure 21:
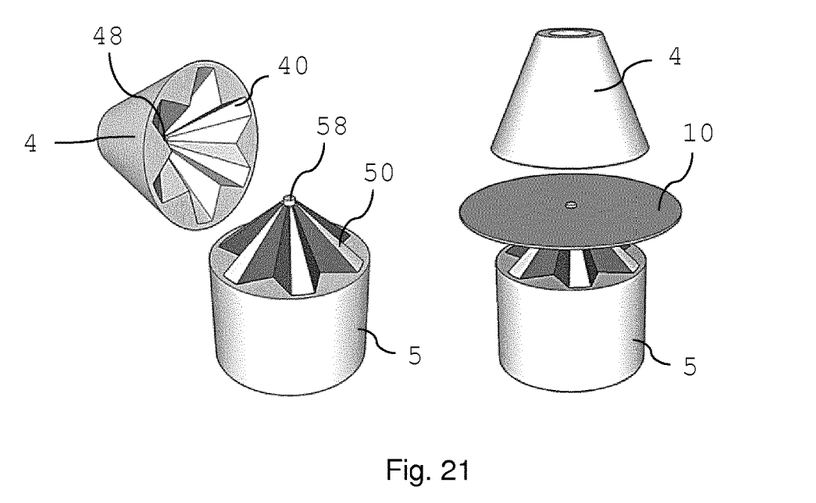
FIG. 21 shows a mouthpiece and body portion comprising centrally arranged alignment and connection elements for a disc-shaped aerosol-generating article.

FIG. 20 and FIG. 21 show embodiments, where the first mould half 50 in the body portion 5 is formed by an internal surface of the body portion protruding from the proximal end of the body portion 5. The second mould half 40 (not shown in FIG. 20) forms a corresponding recess in the mouthpiece portion 4.

In FIG. 21 the first mould half 50 in the form of a protruding star-shaped pyramid is provided with a centrally arranged positioning peg 58. The centrally arranged peg 58 serves to position and align an aerosol-generating article comprising a centrally arranged opening on the first mould half. Such an article may, for example, be a disc 10 as illustrated in FIG. 5. The second mould half 40 comprises a central hole 48 for the peg 58 to be inserted. Central peg 58 and central hole 48 also serve as connection elements for mouthpiece 4 and body portion 5.

Figure 22:
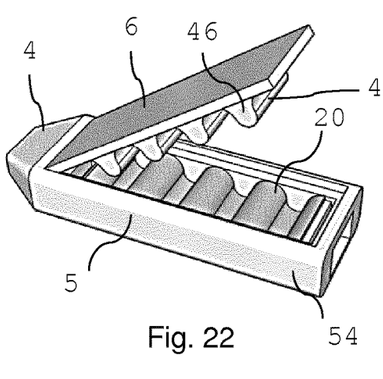
FIG. 22 shows an aerosol-generating device with undulating sheet and device housing with lid.

In FIG. 22 an example of an aerosol-generating device for moulding a corrugated sheet 20 from a flat strip is shown. The body portion 5 of the device has the form of a box 54 comprising a lid 6. The lid 6 basically forms the top of the box 54 and is hingedly connected with the box 54. The moulding cavity for receiving the flat aerosol-generating article basically extends over the entire length and width of the box 54. The internal surface of the lid 6 is provided with a series of perpendicularly arranged undulations 46 forming the second mould half 40. The internal surface of the box 54 is provided with corresponding undulations 56 forming the first mould half 50. Upon closing the lid 6, the flat substrate is formed into the undulating sheet 20.

Figure 23:
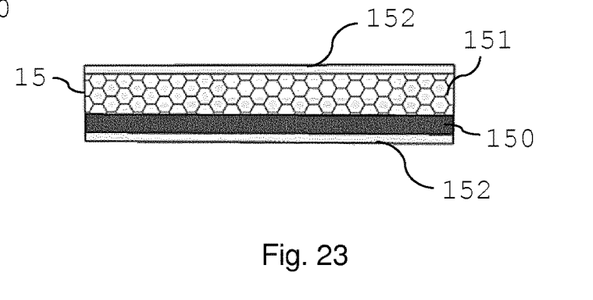
FIG. 23 shows a cross-section of an open, layered aerosol-forming substrate.

FIG. 23 shows a cross section of an open, layered flat aerosol-generating article. The article comprises a layer 150 of an aerosol-forming substrate, preferably a layer of a tobacco containing cast leaf. A second layer 151 is an open layer, for example a mesh arrangement. The open layer 151 allows air and aerosol or evaporated substances from the substrate 150 to enter inside the aerosol-generating article and into the open layer 151 also after the substrate has been transformed into a non-flat article. The article is provided with outer paper layers 152, for example cigarette paper, provided on top of the open layer 151 and below the aerosol-forming substrate layer 150. A thickness of the article may be in a range between 2 mm and 5 mm.

Preferably, a thickness of the paper layers 152 is each between 0.05 mm and 0.2 mm.

Preferably, a thickness of the aerosol-forming substrate layer 150 is between 0.5 mm and 2 mm.

Preferably, a thickness of the open layer 151 is between 1.5 mm and 3 mm.

Preferably, a thickness of the open article 15 is the same as a thickness of a single sheet of aerosol-forming substrate as for example shown in FIG. 1.

Figure 24:
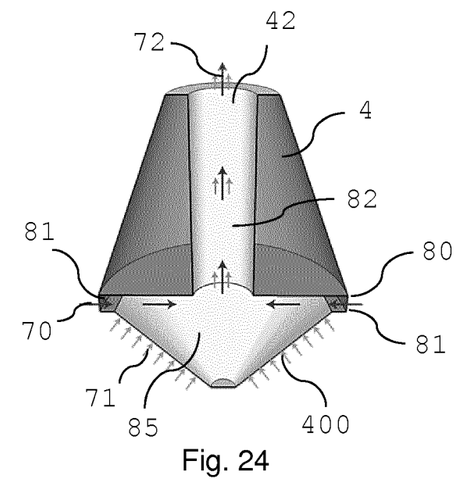
FIGS. 24-27 illustrate embodiments of mouthpieces having a cone-shaped (FIG. 24, 25) or inverse cone-shaped (FIG. 26, 27) mould half with open mould surface.
Figure 25:
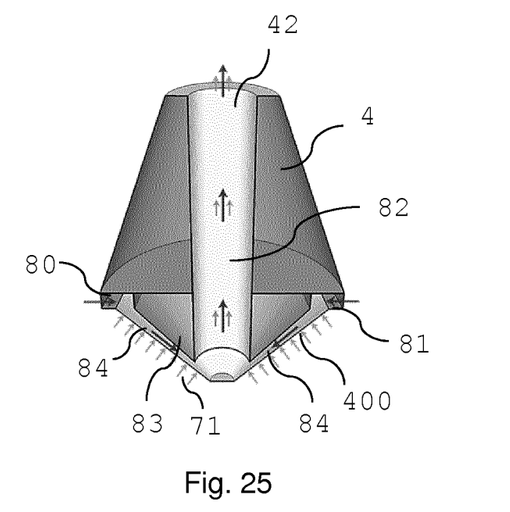
Figure 26:
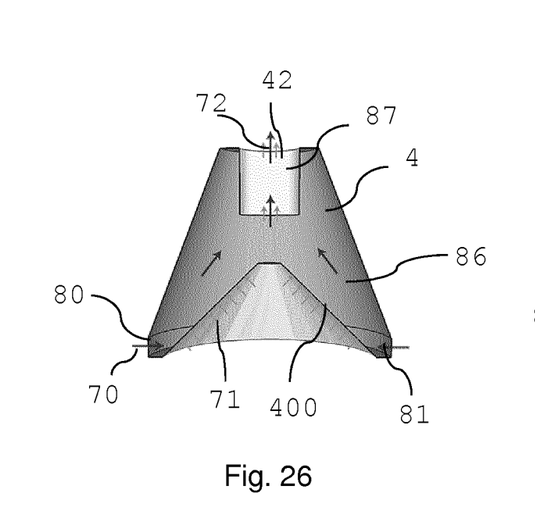
Figure 27:
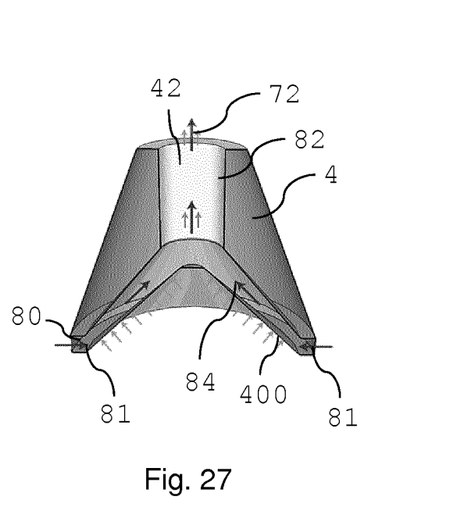

FIGS. 24 to 27 show embodiments of flow management in mouthpiece portions 4, wherein the second mould half is embodied as protruding cone (FIG. 24 and FIG. 25) and wherein the second mould half is embodied as recess (FIG. 26 and FIG. 27.).

In all embodiments the mould surface is porous or provided with openings such that an aerosol or substance evaporated from heated aerosol-forming substrate in the mould may pass through the surface of the second mould half into the mouthpiece and may leave the device via outlet opening 42 arranged at the proximal end of the mouthpiece.

In all embodiments air 70 is drawn from the environment through one or several inlet openings 81 into the mouthpiece. The one or several inlet openings 81 are located around a connection rim 80 of the mouthpiece 4.

In FIG. 24 volatilized substances or aerosol 71 passes through the porous surface 400 of the protruding cone into the interior 85 of the cone. A radially inwardly flowing air flow 70 picks up the aerosol 71 in the interior 85 of the cone. The mixed flow 72 passes in a downstream direction through a centrally arranged conduit 82 in the mouthpiece 4 and leaves the mouthpiece at the outlet opening 42.

In FIG. 25, the interior of the protruding cone comprises a second cone-shaped element 83 also provided with a centrally arranged conduit. The second cone-shaped element 83 is arranged centrally and such as to form a channel 84 between second cone-shaped element 83 and cone surface 400. The entering airflow 70 passes from the openings 81 in the connection rim 80 in the channel 84 versus the top of the protruding cone and via central conduit 82 to the outlet opening 42 of the mouthpiece 4. In the channel 84, the airflow 70 picks up aerosol 71.

In FIG. 26 volatilized substances or aerosol 71 passes through the porous surface 400 of the recessed cone into the interior 86 of the hollow mouthpiece 4. An air flow 70 having entered the mouthpiece 4 at the openings 81 in the connection rim 80 flows downstream and picks up the aerosol 71 in the interior 86 of the mouthpiece. The mixed flow 72 is concentrated to pass into a centrally arranged short conduit 87 in the proximal region of the mouthpiece 4 and leaves the mouthpiece 4 at the outlet opening 42.

In FIG. 27 a channel 84 is arranged along the open cone surface 400 in the interior 86 of the mouthpiece 4. The airflow 70 passes from the openings 81 in the connection rim into the mouthpiece 4 inside the channel 84 versus a centrally arranged conduit 82 and to the outlet opening 42 of the mouthpiece 4.

The invention claimed is:

1. Aerosol-generating device comprising a device housing comprising a moulding cavity for receiving an aerosol-forming substrate,
   the moulding cavity at least partially corresponds to a moulding space between a first and a second mould half of a mould, the first mould half and the second mould half being internal surfaces of the device housing, wherein the internal surfaces of the device housing are formed such that the first mould half is a cavity comprising the shape of an inverse frustum and the second mould half is a correspondingly formed protrusion comprising the shape of a frustum, or vice versa,
   wherein in an open state of the mould corresponding to an open device housing, the aerosol-generating device is adapted to receive a flat aerosol-forming substrate in between the first and second mould halves,
   wherein in a closed state of the mould corresponding to a closed device housing, the moulding space in between the first and second mould halves has a non-flat shape comprising a hollow frustum,
   wherein the first and second mould halves are adapted to transform a flat aerosol-forming substrate supplied between the first and second mould halves into a non-flat aerosol-forming substrate having a shape comprising a hollow frustum corresponding to the non-flat moulding space in the mould upon closing of the mould.

2. Aerosol-generating device according to claim 1, wherein the device housing comprises a mouthpiece and a body portion, the body portion comprising a first internal surface, the mouthpiece comprising a second internal surface having a shape corresponding to the first internal surface of the body portion;

wherein the first internal surface of the body portion is formed as a cavity comprising the shape of an inverse frustum, and wherein the second internal surface of the mouthpiece is formed as a protrusion comprising the shape of a frustum, or vice versa;

the first and second internal surface forming the first and second mould halves, wherein in an assembled state of mouthpiece and body portion the mould is in a closed position forming the moulding space in between the mould halves in the form comprising a hollow frustum.

3. Aerosol-generating device according to claim 2, wherein the first internal surface corresponds to a male mould half comprising a frustum protruding from the device body along a longitudinal axis of the device body, and wherein the second internal surface of the mouthpiece corresponds to a female mould half comprising an inverse frustum, or vice versa.

4. Aerosol-generating device according to claim 2, further comprising alignment elements, for aligning at least one of an aerosol-forming substrate between the mouthpiece and the body portion, or the mouthpiece and the body portion upon assembly of the device housing.

5. Aerosol-generating device according to claim 4, wherein the alignment elements are central alignment elements arranged in a center of the device or wherein the alignment elements are circumferential elements arranged along a circumference of the mouthpiece and of the body portion.

6. Aerosol-generating device according to claim 4, wherein the alignment elements are embodied as connection elements allowing a detachable assembly of the mouthpiece and the body portion.

7. Aerosol-generating device according to claim 1, wherein an internal surface forming a mould half is provided with a plurality of openings enabling aerosol to leave the mould through the internal surface of the mould half provided with the plurality of openings.

8. Aerosol-generating device according to claim 2, wherein an internal surface forming a mould half is provided with a plurality of openings enabling aerosol to leave the mould through the internal surface of the mould half provided with the plurality of openings.

9. Aerosol-generating device according to claim 1, wherein the first or the second mould halves comprise a heating element for heating the transformed non-flat aerosol-forming substrate.

10. Aerosol-generating device according to claim 2, wherein the body portion comprises a heating element arranged on the first internal surface.

11. Aerosol-generating device according to claim 1, wherein the shape of the frustum is one of a circularly conical-shape, a pyramid shaped or a star-shape, and wherein the shape of the inverse frustum is one of an inverse circularly conical-shape, an inverse pyramid shape or an inverse star-shape.

12. Aerosol-generating device according to claim 2, wherein the shape of the frustum is one of a circularly conical-shape, a pyramid shaped or a star-shape, and wherein the shape of the inverse frustum is one of an inverse circularly conical-shape, an inverse pyramid shape or an inverse star-shape.

* * * * *